(12) United States Patent
Cahoon et al.

(10) Patent No.: US 6,251,668 B1
(45) Date of Patent: Jun. 26, 2001

(54) TRANSCRIPTION COACTIVATORS

(75) Inventors: Rebecca E. Cahoon; Hajime Sakai, both of Wilmington; Karlene H. Butler, Newark; J. Antoni Rafalski, Wilmington, all of DE (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 0 days.

(21) Appl. No.: 09/342,084

(22) Filed: Jun. 29, 1999

Related U.S. Application Data

(60) Provisional application No. 60/092,659, filed on Jul. 13, 1998.

(51) Int. Cl.⁷ .............................. C12N 5/00; C07H 21/02; C07K 14/00
(52) U.S. Cl. .................. 435/325; 435/252.3; 435/320.1; 536/23.1; 530/350
(58) Field of Search ................................ 435/69.1, 320.1, 435/252.3, 325; 536/23.1; 530/350

(56) References Cited

FOREIGN PATENT DOCUMENTS

| | | |
|---|---|---|
| 2 150 039 | 8/1996 | (CA) . |
| 0 475 584 | 3/1992 | (EP) . |
| 0 589 841 | 3/1994 | (EP) . |
| WO 93/10250 | 5/1993 | (WO) . |
| WO 99 04004 | 1/1999 | (WO) . |

OTHER PUBLICATIONS

Trienzenberg et al. (1988) Gene Dev. 2:718–729.
Stringer et al., (1990) Nature 345:783–786.
Lin et al., (1991) Nature 353:569–571.
Xiao et al. (1994) Mol. Cell Biol. 14:7013–7024.
Bruhn et al. (1997) Genes Dev. 11(5):640–653.
Hum. Immunol., (1999), 60(1):57–62 (Ref. cited in NCBI General Identifer No. 2896146 submitted in previous IDS).
Uchimiya, H., EMBL—XP002127117—Accession No. D43442 (1998).
Berger, S.L. et al., Cell vol. 70, (1992) pp. 251–265.
Ma, J. et al., Nature, vol. 334 (1988) pp. 631–633.
Bevan et al., Nature, vol. 391, No. 391, pp. 485–488.

*Primary Examiner*—Karen Cochrane Carlson

(57) ABSTRACT

This invention relates to an isolated nucleic acid fragment encoding a transcription coactivator. The invention also relates to the construction of a chimeric gene encoding all or a portion of the transcription coactivator, in sense or antisense orientation, wherein expression of the chimeric gene results in production of altered levels of the transcription coactivator in a transformed host cell.

13 Claims, 1 Drawing Sheet

FIGURE 1

```
                    1                                                          60
SEQ ID NO:2   MAETLDMTLDDIIKNNKKSNPSSRGARRSRGVSAPGGGTGGVGPTRRPFKRAG-------
SEQ ID NO:4   -----------------------------------PPRGPLGLG------------VNSRP
SEQ ID NO:6   MSAAMDMSLDDIIKNNKKSGSGS-----SRGRTRPSGS----GPTRRLPNRAA-------
SEQ ID NO:8   MSSGLNMSLDDLIKQSK----------SRPKANPAFSS--------------GPTRR--
SEQ ID NO:10  ---------HELV-----------------------------------------------
SEQ ID NO:11  MADKMDMSLDDIIKLNR-SQRGGRGGGRGRGRAGSQGGRGGAVQAAARVNRGGGPMRNRP
SEQ ID NO:12  -------------------------GRRGRGRAGSRAGRRGGAQAAARVNRGGGPIRNRP 61                                                         120
SEQ ID NO:2   ------------NRQAPYQPPKAPDAAWQHDMYPAVAAGGGG---GGGRVS--ALETGTK
SEQ ID NO:4   S---------ARTIAKSFSRTKDM--TWRPDLFSDSMAASG-------------IETGTK
SEQ ID NO:6   ------------NRAAPYAPAKAPEATWQHDLYADQHVAAAGYPAQGGRAA--SIETGTK
SEQ ID NO:8   ------AAPSARTMPYPPSAPKAATADSLYGVYSEHVAAMATSPPPPAVAGPQALETGTK
SEQ ID NO:10  --------------------PPESAWQHDMYSDASARGGG----GGRVS--AIETGTK
SEQ ID NO:11  AIARGAAGGG-RNRPAPYSRPKQLPDKWQHDLF------DSGFGGGAG------VETGGK
SEQ ID NO:12  AIARGAAGGGGRNRPAPYSRPKQLPDKWQHDLF------DSGFGGGAG------VETGGK 121                                                        180
SEQ ID NO:2   LYISNLDFGVSNDDIKELFSELGDLKRFSIIYDRSGRSKGTAEVVFARRSDAVAAVKKYN
SEQ ID NO:4   LYISNLDYGVSNEDIKELFSEVGHLKRFAVHFDGYGRPNGTAEVVFTRRSDAIAALKRYN
SEQ ID NO:6   LYISNLDYGVSNDDIKELFAEVGDLKRHAVHYDRSGKXKGTTEVVFSRRADAVSAVKRYN
SEQ ID NO:8   LHISNLDSSVTVEDVQELFSEIGELKRYSVNYDRMGSLREVREVVFARKVDALDAIERYN
SEQ ID NO:10  LLITNLDFGVSTEDLKELFSELGDVKRCLIHYDRSGRSKGTAEVIFARRGDAVAALRKYN
SEQ ID NO:11  LLVSNLDFGVSDADIQELFAEFGTLKKAAVHYDRSGRSLGTADVHFERKADALKAMKQYN
SEQ ID NO:12  LLVSNLDFGVSDADIQELFAEFGTLKKAAVHYDRSGRSLGTANVHFERKADALKAMKQYN 181                                                        240
SEQ ID NO:2   NVQLDGKPMKIEIVGTNTP---TASAALPVSNGGHARNAVRSAPRGAAPAGVPQRRPHQR
SEQ ID NO:4   NVLLDGKAMKIEVIGSDLGLPMTPRINVVGASNGRPTRTVVMTPEIGQRGSGSSSRPTGP
SEQ ID NO:6   NVQLDGKPMKIEIVGTNI------------------------------------------
SEQ ID NO:8   GVLLDGKPMKIELIGKXTE-----PHPTDPLMYNGTFSNYNAMPNSLLQRGG-----PRGP
SEQ ID NO:10  NVQLDGKPMKIEILGTNTP---TAPAALPTNNGTYARNVAKSAPRGVS-ASLPQNRPRAR
SEQ ID NO:11  GVPLDGRPMNIQLVTSQI------------------DTQRRPAQSINRGGMT-------
SEQ ID NO:12  GFPLDGRPMNIQLVTSQI------------------DAQRRPAQSVNRGGMT-------

241                                                        300
SEQ ID NO:2   GGR--RSGGSG---GGRRGKERTS-----QSRLKNSTLTWRSIMLMRCRPTKCVHKFDIQ
SEQ ID NO:4   TVNRYNRGAFQAGRGRGRGRGRAPFQSQFQGRGTGSVRG-RGQFQGRGRGRRQAGK--TA
SEQ ID NO:6   ------------------------------------------------------------
SEQ ID NO:8   FHGNGRSGGSGQGGAGKRGM----FQGNVRPGNTVQDGGGRGQ--GRARGHDRSRVPTSA
SEQ ID NO:10  GGRGRRGGGGSGSGGRRGKER-S-----QPR---------------------------SA
SEQ ID NO:11  --RNRGSGGFGGGG-TRRGTRGGS-----RGRGRGTGRNSKQQL--------------SA
SEQ ID NO:12  --RNRGAGGFGGGGGTRRGTRGGA-----RGRGRGAGRNSKQQL--------------SA 301                                      347
SEQ ID NO:2   HQISSTLVLPFQLFVLLCSGDNKPYVCGGIALLNFVGFVYNRTRVG.
SEQ ID NO:4   DELDKDLE---------------TYHAEAM-------------KTD.
SEQ ID NO:6   ----------------------------------------------S
SEQ ID NO:8   ADLDAELE---------------QYHAAAV-------------KQK.
SEQ ID NO:10  EELDAEL----------------EKYHAQGTTPMQ---------TTE.
SEQ ID NO:11  EELDAQLD---------------------------AYNARMDTS
SEQ ID NO:12  EELDAQLD---------------------------AYNARMDTS
```

SEQUENCE LISTING

<160> NUMBER OF SEQ ID NOS: 12

<210> SEQ ID NO: 1
<211> LENGTH: 1127
<212> TYPE: DNA
<213> ORGANISM: Zea mays

<400> SEQUENCE: 1

```
gcacgaggcc tttcccagcc aaaagaaata tccaattcct caccctaccc cctcgctgct      60
ttctcctccc cgtcgacctc gccaatcttc ctcccgctaa ccctagtcca gcacccgaga     120
tctactccgc gcaaacagcc atggcggaga cgctcgacat gaccctcgac gacatcatca     180
agaacaacaa gaagagtaac ccctcgtctc gcggggcccg ccgcagccgc ggcgtatccg     240
cccctggcgg cgggaccggc ggggtcgggc cgaccaggcg ccccttaaa  agggctggga     300 acaggcaggc gccctaccag ccgccgaagg ccccgacgc  tgcgtggcag cacgacatgt     360
accctgcggt cgccgcagga ggaggcggcg gcggcgggag ggtctcggcg ctcgagacgg     420
gcaccaagct ctacatctcc aacctggact ttgggtttc  gaacgacgat atcaaggagc     480
tgttctctga gctaggtgat ctgaagcgtt tttcgataat atatgatcga agtgggaggt     540
ctaagggaac agctgaagtt gtatttgcaa ggcgttctga tgctgtagcg gcggtgaaga     600
aatataacaa tgtccaactt gatggtaagc ccatgaagat agagatagtt gggaccaata     660
ctccaactgc atctgctgct cttccagtct ccaatggtgg ccatgctagg aatgctgtga     720
ggagtgcacc gaggggtgct gccccagcag gtgtgccgca gcgaagacct catcagaggg     780
gtgggaggcg tagtggtgga tctggggggtg gtcgtcgtgg caaggagcgc acaagccaaa     840
gtcggctgaa gaactcgacg ctgacttgga gaagtatcat gctgatgcga tgcagaccaa     900
ctaaatgtgt tcacaaattt gatattcaac atcaaatatc aagcacatta gtccttccat     960
```

```
tccagctgtt tgtgctacta tgttcagggg acaacaaacc ttatgtttgt gggggtattg    1020
ctttactgaa ttttgtgggt tttgtttaca atagaactag agttggatga tgctgagtac    1080
ttccatggaa attacttgct tgcctttaaa aaaaaaaaaa aaaaaac                  1127
```

<210> SEQ ID NO: 2
<211> LENGTH: 309
<212> TYPE: PRT
<213> ORGANISM: Zea mays

<400> SEQUENCE: 2

```
Met Ala Glu Thr Leu Asp Met Thr Leu Asp Ile Ile Lys Asn Asn
 1               5                  10                  15

Lys Lys Ser Asn Pro Ser Ser Arg Gly Ala Arg Ser Arg Gly Val
                20                  25                  30

Ser Ala Pro Gly Gly Thr Gly Val Gly Pro Thr Arg Arg Pro
            35                  40                  45

Phe Lys Arg Ala Gly Asn Arg Gln Ala Pro Tyr Gln Pro Pro Lys Ala
 50                  55                  60

Pro Asp Ala Ala Trp Gln His Asp Met Tyr Pro Ala Val Ala Ala Gly
 65                  70                  75                  80

Gly Gly Gly Gly Gly Arg Val Ser Ala Leu Glu Thr Gly Thr Lys
                85                  90                  95

Leu Tyr Ile Ser Asn Leu Asp Phe Gly Val Ser Asn Asp Ile Lys
                100                 105                 110

Glu Leu Phe Ser Glu Leu Gly Asp Leu Lys Arg Phe Ser Ile Ile Tyr
                115                 120                 125

Asp Arg Ser Gly Arg Ser Lys Gly Thr Ala Glu Val Val Phe Ala Arg
130                 135                 140

Arg Ser Asp Ala Val Ala Ala Val Lys Lys Tyr Asn Asn Val Gln Leu
145                 150                 155                 160

Asp Gly Lys Pro Met Lys Ile Glu Ile Val Gly Thr Asn Thr Pro Thr
                165                 170                 175

Ala Ser Ala Ala Leu Pro Val Ser Asn Gly Gly His Ala Arg Asn Ala
                180                 185                 190

Val Arg Ser Ala Pro Arg Gly Ala Ala Pro Ala Gly Val Pro Gln Arg
                195                 200                 205

Arg Pro His Gln Arg Gly Gly Arg Ser Gly Gly Ser Gly Gly Gly
210                 215                 220

Arg Arg Gly Lys Glu Arg Thr Ser Gln Ser Arg Leu Lys Asn Ser Thr
225                 230                 235                 240

Leu Thr Trp Arg Ser Ile Met Leu Met Arg Cys Arg Pro Thr Lys Cys
                245                 250                 255

Val His Lys Phe Asp Ile Gln His Gln Ile Ser Ser Thr Leu Val Leu
                260                 265                 270

Pro Phe Gln Leu Phe Val Leu Leu Cys Ser Gly Asp Asn Lys Pro Tyr
                275                 280                 285

Val Cys Gly Gly Ile Ala Leu Leu Asn Phe Val Gly Phe Val Tyr Asn
            290                 295                 300

Arg Thr Arg Val Gly
305
```

<210> SEQ ID NO: 3
<211> LENGTH: 947
<212> TYPE: DNA
<213> ORGANISM: Oryza sativa

<400> SEQUENCE: 3

```
gcacgagggc gtacctcctc gagggcccct tggcctcggg gttaactcgc ggccatcagc    60
gcgcactatt gctaagtctt ttagcagaac caaagacatg acctggagac ctgatctgtt   120
tagtgatagt atggcagcta gtggaattga aactggtaca aaattgtaca tttcaaactt   180
ggactatggg gtttccaatg aggatataaa ggagctgttt tcagaagttg gtcacttgaa   240
gcgctttgct gttcactttg atggttatgg gcgcccaaat ggcacagcag aagtggtgtt   300
tactaggaga agtgatgcaa ttgctgcatt gaaacgttac aataatgttc tgcttgatgg   360
taaagctatg aagatagaag ttattggaag tgacttaggt ttgcctatga cacctcgcat   420
aaatgtggtt ggggcttcta atggcagacc tacaagaaca gttgttatga cgcctgaaat   480
tggccagcgt ggcagtggtt ccagcagtag accaacaggt cctacagtta atagatataa   540
ccgtggtgcc ttccaagctg gccggggccg aggccgtggc aggggtcgtg ccccattcca   600
gtcccagttc cagggccgtg gcactggcag tgtcaggggc cgtggtcaat tccagggccg   660
tggtcgcgga aggaggcaag ctgggaagac tgcagatgag ctggacaaag acctggaaac   720
ttatcatgct gaggcaatga agaccgactg atcgctgcag acctaacggt ggtggcagcc   780
attttgtcac aactgctcta taagcatctg ttgcaagatt atcgttatga taggttagcc   840
cgattgagct gtagtactcc tggaagcaga gaactttctg cttaggtttg caaaacaaa    900
ctctgcctct agaagtttga agaagacgca aaaaaaaaa aaaaaaa                  947
```

<210> SEQ ID NO: 4
<211> LENGTH: 245
<212> TYPE: PRT
<213> ORGANISM: Oryza sativa

<400> SEQUENCE: 4

```
Pro Pro Arg Gly Pro Leu Gly Leu Gly Val Asn Ser Arg Pro Ser Ala
  1               5                  10                  15

Arg Thr Ile Ala Lys Ser Phe Ser Arg Thr Lys Asp Met Thr Trp Arg
             20                  25                  30

Pro Asp Leu Phe Ser Asp Ser Met Ala Ala Ser Gly Ile Glu Thr Gly
         35                  40                  45

Thr Lys Leu Tyr Ile Ser Asn Leu Asp Tyr Gly Val Ser Asn Glu Asp
     50                  55                  60

Ile Lys Glu Leu Phe Ser Glu Val Gly His Leu Lys Arg Phe Ala Val
 65                  70                  75                  80

His Phe Asp Gly Tyr Gly Arg Pro Asn Gly Thr Ala Glu Val Val Phe
                 85                  90                  95

Thr Arg Arg Ser Asp Ala Ile Ala Ala Leu Lys Arg Tyr Asn Asn Val
            100                 105                 110

Leu Leu Asp Gly Lys Ala Met Lys Ile Glu Val Ile Gly Ser Asp Leu
        115                 120                 125

Gly Leu Pro Met Thr Pro Arg Ile Asn Val Val Gly Ala Ser Asn Gly
    130                 135                 140

Arg Pro Thr Arg Thr Val Val Met Thr Pro Glu Ile Gly Gln Arg Gly
145                 150                 155                 160

Ser Gly Ser Ser Ser Arg Pro Thr Gly Pro Thr Val Asn Arg Tyr Asn
                165                 170                 175

Arg Gly Ala Phe Gln Ala Gly Arg Gly Arg Gly Arg Gly Arg
            180                 185                 190
```

```
Ala Pro Phe Gln Ser Gln Phe Gln Gly Arg Gly Thr Gly Ser Val Arg
            195                 200                 205

Gly Arg Gly Gln Phe Gln Gly Arg Gly Arg Gly Arg Gln Ala Gly
        210                 215                 220

Lys Thr Ala Asp Glu Leu Asp Lys Asp Leu Glu Thr Tyr His Ala Glu
225                 230                 235                 240

Ala Met Lys Thr Asp
                245

<210> SEQ ID NO: 5
<211> LENGTH: 730
<212> TYPE: DNA
<213> ORGANISM: Glycine max
<220> FEATURE:
<221> NAME/KEY: unsure
<222> LOCATION: (523)
<220> FEATURE:
<221> NAME/KEY: unsure
<222> LOCATION: (692)
<220> FEATURE:
<221> NAME/KEY: unsure
<222> LOCATION: (707)
<220> FEATURE:
<221> NAME/KEY: unsure
<222> LOCATION: (726)

<400> SEQUENCE: 5
ggaagcctta aatctatcat atcaccagcc acccttctcc cgtatctcac ttcctcgacg    60
aaaccctaag cttcccctttt ctttcactct catcagatcc tttcgtcgtt gcgcgaaacc   120
ctatctctga accagcaaac atgtctgcag ccatggatat gtcgctcgac gacataatca   180
agaacaacaa aaagtctgga tccggaagtt cacgtggccg acccgaccc tccggatccg    240 gacctactcg ccggctcccc aaccgtgccg ccaaccgcgc cgcacttat gccccgcta    300 aggcgccgga ggcaacgtgg cagcacgatt tatatgcaga tcagcatgtg gctgcggcgg   360
ggtaccctgc tcaaggtggt cgtgcggctt ccatagaaac tgggaccaag ctttacattt    420
caaacttgga ttatggtgtt tccaatgatg atattaagga attgtttgct gaagtgggtg   480
acttgaaacg gcatgcggtt cattatgaca ggagtggcaa atnaaagggt acaacagaag   540
tagtattttc acgacgagct gatgctgtat ctgctgtaaa gagatacaac aatgttcaat   600
tggatgggaa accaatgaag attgagattg tgggaaccaa catttccaca cctgggtgtt   660
ggctcctgcc cctaacgggg ctaattggaa antttgatgg agttccncca agtggacaaa    720 gaagangtgg                                                          730

<210> SEQ ID NO: 6
<211> LENGTH: 169
<212> TYPE: PRT
<213> ORGANISM: Glycine max
<220> FEATURE:
<221> NAME/KEY: UNSURE
<222> LOCATION: (128)

<400> SEQUENCE: 6

Met Ser Ala Ala Met Asp Met Ser Leu Asp Asp Ile Ile Lys Asn Asn
  1               5                  10                  15

Lys Lys Ser Gly Ser Gly Ser Ser Arg Gly Arg Thr Arg Pro Ser Gly
            20                  25                  30

Ser Gly Pro Thr Arg Arg Leu Pro Asn Arg Ala Ala Asn Arg Ala Ala
        35                  40                  45

Pro Tyr Ala Pro Ala Lys Ala Pro Glu Ala Thr Trp Gln His Asp Leu
```

-continued

```
            50                  55                  60
Tyr Ala Asp Gln His Val Ala Ala Gly Tyr Pro Ala Gln Gly Gly
 65                  70                  75                  80

Arg Ala Ala Ser Ile Glu Thr Gly Thr Lys Leu Tyr Ile Ser Asn Leu
                 85                  90                  95

Asp Tyr Gly Val Ser Asn Asp Ile Lys Glu Leu Phe Ala Glu Val
            100                 105                 110

Gly Asp Leu Lys Arg His Ala Val His Tyr Asp Arg Ser Gly Lys Xaa
            115                 120                 125

Lys Gly Thr Thr Glu Val Val Phe Ser Arg Arg Ala Asp Ala Val Ser
        130                 135                 140

Ala Val Lys Arg Tyr Asn Asn Val Gln Leu Asp Gly Lys Pro Met Lys
145                 150                 155                 160

Ile Glu Ile Val Gly Thr Asn Ile Ser
                165
```

<210> SEQ ID NO: 7
<211> LENGTH: 1110
<212> TYPE: DNA
<213> ORGANISM: Triticum aestivum

<400> SEQUENCE: 7

```
gcacgagcct catccttgcc ttagttttag acgccggcgc cgtagagccc gttccccctc     60
acgcggccag cgaccatgtc gagtggcctg aacatgtccc tagatgacct catcaagcaa    120
tccaagtcca ggcccaaagc caaccccgcc ttctcttccg ggcccacccg ccgggcggcg    180
ccgtccgccc ggaccatgcc ctaccgcgcc tctgctccca aggccgccac cgccgactct    240
ctgtacggtg tctactccga gcacgttgcc gccatggcaa cctcccgcc accgccggcg    300
gtggccgggc acaggcact cgagacgggc acgaagctgc acatctccaa cctcgactcc    360
agcgtcaccg tcgaggacgt ccaggaactc ttttcagaga ttggtgagct caaacgttat    420
tctgttaact acgataggat gggaagtctc agggaagtgc gggaagttgt ctttgcaaga    480
aaagtagatg ctttggatgc tattgagaga tataatggtg ttctgcttga tgggaagcca    540
atgaagatag agctcattgg gaaatagacc gagccacacc caacagaccc tttgatgtac    600
aacggcactt tttctaacta caatgcaatg ccaaacagtc tgcttcagag aggtggcccg    660
agaggcccat ttcatggtaa tggtcgttct ggaggcagtg gtcagggcgg tgctggcaaa    720
agaggaatgt ttcaaggcaa cgttcgtcct ggaaacactg tccaggacgg tggtgggcgg    780
ggacagggta gagccagggg gcatgatcgc agccgagttc cgacctctgc tgcggatctt    840
gatgctgaac tggagcagta tcatgcagca gcagtgaagc aaaaatgagg ctctgagtat    900
atacatagac tgttgcatta ttagtttcct gcttttagtc gtcaggtacc atgttgagaa    960
aagttggaag gcattaattc gacatttaca tctgctgcgc tttttatatc cctactccga   1020
gtgctggata tattgtatta cctaattttg aaacatgggt gttctcttgg ggtttatttg   1080
gatagtaaga ttaaaaaaaa aaaaaaaaaa                                    1110
```

<210> SEQ ID NO: 8
<211> LENGTH: 270
<212> TYPE: PRT
<213> ORGANISM: Triticum aestivum
<220> FEATURE:
<221> NAME/KEY: UNSURE
<222> LOCATION: (164)

<400> SEQUENCE: 8

| Met | Ser | Ser | Gly | Leu | Asn | Met | Ser | Leu | Asp | Asp | Leu | Ile | Lys | Gln | Ser |
| 1 | | | | 5 | | | | | 10 | | | | | 15 | |

| Lys | Ser | Arg | Pro | Lys | Ala | Asn | Pro | Ala | Phe | Ser | Ser | Gly | Pro | Thr | Arg |
| | | | 20 | | | | | 25 | | | | | 30 | | |

| Arg | Ala | Ala | Pro | Ser | Ala | Arg | Thr | Met | Pro | Tyr | Pro | Pro | Ser | Ala | Pro |
| | | 35 | | | | | 40 | | | | | 45 | | | |

| Lys | Ala | Ala | Thr | Ala | Asp | Ser | Leu | Tyr | Gly | Val | Tyr | Ser | Glu | His | Val |
| | 50 | | | | | 55 | | | | | 60 | | | | |

| Ala | Ala | Met | Ala | Thr | Ser | Pro | Pro | Pro | Ala | Val | Ala | Gly | Pro | Gln | |
| 65 | | | | | 70 | | | | | 75 | | | | | 80 |

| Ala | Leu | Glu | Thr | Gly | Thr | Lys | Leu | His | Ile | Ser | Asn | Leu | Asp | Ser | Ser |
| | | | | 85 | | | | | 90 | | | | | 95 | |

| Val | Thr | Val | Glu | Asp | Val | Gln | Glu | Leu | Phe | Ser | Glu | Ile | Gly | Glu | Leu |
| | | | | 100 | | | | | 105 | | | | | 110 | |

| Lys | Arg | Tyr | Ser | Val | Asn | Tyr | Asp | Arg | Met | Gly | Ser | Leu | Arg | Glu | Val |
| | | | 115 | | | | | 120 | | | | | 125 | | |

| Arg | Glu | Val | Val | Phe | Ala | Arg | Lys | Val | Asp | Ala | Leu | Asp | Ala | Ile | Glu |
| | 130 | | | | | 135 | | | | | 140 | | | | |

| Arg | Tyr | Asn | Gly | Val | Leu | Leu | Asp | Gly | Lys | Pro | Met | Lys | Ile | Glu | Leu |
| 145 | | | | 150 | | | | | 155 | | | | | 160 | |

| Ile | Gly | Lys | Xaa | Thr | Glu | Pro | His | Pro | Thr | Asp | Pro | Leu | Met | Tyr | Asn |
| | | | | 165 | | | | | 170 | | | | | 175 | |

| Gly | Thr | Phe | Ser | Asn | Tyr | Asn | Ala | Met | Pro | Asn | Ser | Leu | Leu | Gln | Arg |
| | | | 180 | | | | | 185 | | | | | 190 | | |

| Gly | Gly | Pro | Arg | Gly | Pro | Phe | His | Gly | Asn | Arg | Ser | Gly | Gly | Ser | |
| | | 195 | | | | | 200 | | | | | 205 | | | |

| Gly | Gln | Gly | Gly | Ala | Gly | Lys | Arg | Gly | Met | Phe | Gln | Gly | Asn | Val | Arg |
| | 210 | | | | | 215 | | | | | 220 | | | | |

| Pro | Gly | Asn | Thr | Val | Gln | Asp | Gly | Gly | Arg | Gly | Gln | Gly | Arg | Ala | |
| 225 | | | | | 230 | | | | | 235 | | | | | 240 |

| Arg | Gly | His | Asp | Arg | Ser | Arg | Val | Pro | Thr | Ser | Ala | Ala | Asp | Leu | Asp |
| | | | 245 | | | | | 250 | | | | | 255 | | |

| Ala | Glu | Leu | Glu | Gln | Tyr | His | Ala | Ala | Ala | Val | Lys | Gln | Lys | | |
| | 260 | | | | | 265 | | | | | 270 | | | | |

<210> SEQ ID NO: 9
<211> LENGTH: 919
<212> TYPE: DNA
<213> ORGANISM: Triticum aestivum

<400> SEQUENCE: 9

```
gcacgagctc gtgccgccgg aatcggcgtg gcagcacgac atgtactctg acgcctctgc      60
cagaggcggc ggcggcggga gggtctctgc tatcgagacc ggcaccaagc tcctcatcac     120
caatttggac ttcggcgtct caaccgagga cctcaaggag cttttctccg agctgggtga     180
tgtgaagcga tgcttgattc actatgaccg aagtgggagg tctaagggaa cagctgaggt     240
tatatttgca aggcgtggtg atgctgttgc agcgctgagg aaatacaaca atgtccaact     300
tgatggcaag cctatgaaaa tagagatact tgggactaac actcctactg ctccagctgc     360
actaccaacc aataatggaa cctatgctag gaatgttgct aagagtgcac caagggggtgt     420
ctcagctagt ttgccacaga acagaccccg tgcaagggggt gggaggggtc gtcgtggtgg     480
tggcggaggc agtggatctg gcggtcgtcg tgggaaagagc cgtagccagc caaggtctgc     540
tgaagaactt gatgctgagt tggagaagta ccatgcacag ggtacgacgc cgatgcagac     600
```

-continued

```
caccgaataa atcgacatct ttgcagcgtt gatattcaac atgaaatttg aagggtgccc     660
ctttgttccc gcttttgtg ctactatatg ttcaagggac aacaaaacct tttacttgtc      720
aggttcttgg cttactgaat tgtatggtt atgtgtctac atagaactag agttgagtgg      780
ataccggtga acactactgt tatgaacatt acttgattgc ctttagtttc tgccttcctt     840
gaggagcgca aggactaagg accacccaag ttgctccgca tgtgaaagtt attgaagatg     900
tatgaggtgc tcaaaaaaa                                                  919
```

<210> SEQ ID NO: 10
<211> LENGTH: 202
<212> TYPE: PRT
<213> ORGANISM: Triticum aestivum

<400> SEQUENCE: 10

| | | | | | | | | | | | | | | |
|---|---|---|---|---|---|---|---|---|---|---|---|---|---|---|
| His | Glu | Leu | Val | Pro | Pro | Glu | Ser | Ala | Trp | Gln | His | Asp | Met | Tyr | Ser |
| 1 | | | | 5 | | | | | 10 | | | | | 15 | |
| Asp | Ala | Ser | Ala | Arg | Gly | Gly | Gly | Gly | Arg | Val | Ser | Ala | Ile | Glu |
| | | | 20 | | | | 25 | | | | | 30 | | |
| Thr | Gly | Thr | Lys | Leu | Leu | Ile | Thr | Asn | Leu | Asp | Phe | Gly | Val | Ser | Thr |
| | | 35 | | | | | 40 | | | | | 45 | | | |
| Glu | Asp | Leu | Lys | Glu | Leu | Phe | Ser | Glu | Leu | Gly | Asp | Val | Lys | Arg | Cys |
| 50 | | | | | 55 | | | | | 60 | | | | | |
| Leu | Ile | His | Tyr | Asp | Arg | Ser | Gly | Arg | Ser | Lys | Gly | Thr | Ala | Glu | Val |
| 65 | | | | 70 | | | | | 75 | | | | | 80 | |
| Ile | Phe | Ala | Arg | Arg | Gly | Asp | Ala | Val | Ala | Ala | Leu | Arg | Lys | Tyr | Asn |
| | | | | 85 | | | | | 90 | | | | | 95 | |
| Asn | Val | Gln | Leu | Asp | Gly | Lys | Pro | Met | Lys | Ile | Glu | Ile | Leu | Gly | Thr |
| | | | 100 | | | | | 105 | | | | | 110 | | |
| Asn | Thr | Pro | Thr | Ala | Pro | Ala | Ala | Leu | Pro | Thr | Asn | Asn | Gly | Thr | Tyr |
| | | | 115 | | | | | 120 | | | | | 125 | | |
| Ala | Arg | Asn | Val | Ala | Lys | Ser | Ala | Pro | Arg | Gly | Val | Ser | Ala | Ser | Leu |
| | 130 | | | | | 135 | | | | | 140 | | | | |
| Pro | Gln | Asn | Arg | Pro | Arg | Ala | Arg | Gly | Gly | Arg | Gly | Arg | Arg | Gly | Gly |
| 145 | | | | | 150 | | | | | 155 | | | | | 160 |
| Gly | Gly | Gly | Ser | Gly | Ser | Gly | Gly | Arg | Gly | Lys | Glu | Arg | Ser | Gln |
| | | | | 165 | | | | | 170 | | | | | 175 | |
| Pro | Arg | Ser | Ala | Glu | Glu | Leu | Asp | Ala | Glu | Leu | Glu | Lys | Tyr | His | Ala |
| | | | 180 | | | | | 185 | | | | | 190 | | |
| Gln | Gly | Thr | Thr | Pro | Met | Gln | Thr | Thr | Glu |
| | | | 195 | | | | | 200 | |

<210> SEQ ID NO: 11
<211> LENGTH: 255
<212> TYPE: PRT
<213> ORGANISM: Mus musculus

<400> SEQUENCE: 11

| | | | | | | | | | | | | | | |
|---|---|---|---|---|---|---|---|---|---|---|---|---|---|---|---|
| Met | Ala | Asp | Lys | Met | Asp | Met | Ser | Leu | Asp | Asp | Ile | Ile | Lys | Leu | Asn |
| 1 | | | | 5 | | | | | 10 | | | | | 15 | |
| Arg | Ser | Gln | Arg | Gly | Gly | Arg | Gly | Gly | Arg | Gly | Arg | Gly | Arg | Ala |
| | | | 20 | | | | 25 | | | | | 30 | | |
| Gly | Ser | Gln | Gly | Gly | Arg | Gly | Gly | Ala | Val | Gln | Ala | Ala | Ala | Arg | Val |
| | | 35 | | | | | 40 | | | | | 45 | | | |
| Asn | Arg | Gly | Gly | Gly | Pro | Met | Arg | Asn | Arg | Pro | Ala | Ile | Ala | Arg | Gly |
| | 50 | | | | | 55 | | | | | 60 | | | | |

-continued

```
Ala Ala Gly Gly Gly Arg Asn Arg Pro Ala Pro Tyr Ser Arg Pro Lys
 65                  70                  75                  80

Gln Leu Pro Asp Lys Trp Gln His Asp Leu Phe Asp Ser Gly Phe Gly
                 85                  90                  95

Gly Gly Ala Gly Val Glu Thr Gly Gly Lys Leu Leu Val Ser Asn Leu
            100                 105                 110

Asp Phe Gly Val Ser Asp Ala Asp Ile Gln Glu Leu Phe Ala Glu Phe
        115                 120                 125

Gly Thr Leu Lys Lys Ala Ala Val His Tyr Asp Arg Ser Gly Arg Ser
    130                 135                 140

Leu Gly Thr Ala Asp Val His Phe Glu Arg Lys Ala Asp Ala Leu Lys
145                 150                 155                 160

Ala Met Lys Gln Tyr Asn Gly Val Pro Leu Asp Gly Arg Pro Met Asn
                165                 170                 175

Ile Gln Leu Val Thr Ser Gln Ile Asp Thr Gln Arg Arg Pro Ala Gln
            180                 185                 190

Ser Ile Asn Arg Gly Gly Met Thr Arg Asn Arg Gly Ser Gly Gly Phe
        195                 200                 205

Gly Gly Gly Gly Thr Arg Arg Gly Thr Arg Gly Gly Ser Arg Gly Arg
    210                 215                 220

Gly Arg Gly Thr Gly Arg Asn Ser Lys Gln Gln Leu Ser Ala Glu Glu
225                 230                 235                 240

Leu Asp Ala Gln Leu Asp Ala Tyr Asn Ala Arg Met Asp Thr Ser
                245                 250                 255

<210> SEQ ID NO: 12
<211> LENGTH: 233
<212> TYPE: PRT
<213> ORGANISM: Homo sapiens

<400> SEQUENCE: 12

Gly Arg Arg Gly Arg Gly Arg Ala Gly Ser Arg Ala Gly Arg Arg Gly
 1               5                  10                  15

Gly Ala Gln Ala Ala Ala Arg Val Asn Arg Gly Gly Pro Ile Arg
             20                  25                  30

Asn Arg Pro Ala Ile Ala Arg Gly Ala Ala Gly Gly Gly Arg Asn
         35                  40                  45

Arg Pro Ala Pro Tyr Ser Arg Pro Lys Gln Leu Pro Asp Lys Trp Gln
    50                  55                  60

His Asp Leu Phe Asp Ser Gly Phe Gly Gly Ala Gly Val Glu Thr
 65                  70                  75                  80

Gly Gly Lys Leu Leu Val Ser Asn Leu Asp Phe Gly Val Ser Asp Ala
                 85                  90                  95

Asp Ile Gln Glu Leu Phe Ala Glu Phe Gly Thr Leu Lys Lys Ala Ala
            100                 105                 110

Val His Tyr Asp Arg Ser Gly Arg Ser Leu Gly Thr Ala Asn Val His
        115                 120                 125

Phe Glu Arg Lys Ala Asp Ala Leu Lys Ala Met Lys Gln Tyr Asn Gly
    130                 135                 140

Phe Pro Leu Asp Gly Arg Pro Met Asn Ile Gln Leu Val Thr Ser Gln
145                 150                 155                 160

Ile Asp Ala Gln Arg Arg Pro Ala Gln Ser Val Asn Arg Gly Gly Met
                165                 170                 175

Thr Arg Asn Arg Gly Ala Gly Gly Phe Gly Gly Gly Gly Thr Arg
```

-continued

```
                  180                 185                 190
Arg Gly Thr Arg Gly Gly Ala Arg Gly Arg Gly Arg Gly Ala Gly Arg
            195                 200                 205
Asn Ser Lys Gln Gln Leu Ser Ala Glu Glu Leu Asp Ala Gln Leu Asp
        210                 215                 220
Ala Tyr Asn Ala Arg Met Asp Thr Ser
225                 230
```

US 6,251,668 B1

TRANSCRIPTION COACTIVATORS

This application claims the benefit of U.S. Provisional Application No. 60/092,659, filed Jul. 13, 1998.

FIELD OF THE INVENTION

This invention is in the field of plant molecular biology. More specifically, this invention pertains to nucleic acid fragments encoding transcription coactivators in plants and seeds.

BACKGROUND OF THE INVENTION

In eukaryotes transcription initiation requires the action of several proteins acting in concert to initiate mRNA production. Two cis-acting regions of DNA have been identified that bind transcription initiation proteins. The first binding site located approximately 25–30 bp upstream of the transcription initiation site is termed the TATA box. The second region of DNA required for transcription initiation is the upstream activation site (UAS) or enhancer region. This region of DNA is somewhat distal from the TATA box. During transcription initiation RNA polymerase II is directed to the TATA box by general transcription factors. Transcription activators which have both a DNA binding domain and an activation domain bind to the UAS region and stimulate transcription initiation by physically interacting with the general transcription factors and RNA polymerase. Direct physical interactions have been demonstrated between activators and general transcription factors in vitro, such as between the acidic activation domain of herpes simplex virus VP 16 and TATA-binding protein (TBP), TFIIB, or TFIIH (Triezenberg et al. (1988) *Gene Dev.* 2:718–729; Stringer et al. (1990) *Nature* 345:783–786; Lin et al. (1991) *Nature* 353:569–571; Xiao et al. (1994) *Mol. Cell. Biol.* 14:7013–7024).

A third factor that is involved in the interaction is the adaptor proteins. It is thought that adaptor proteins serve to mediate the interaction between transcriptional activators and general transcription factors. Functional and physical interactions have also been demonstrated between the activators and various transcription coactivators. These transcription coactivators normally can not bind to DNA directly, however they can "bridge" the interaction between transcription activators and general transcription factors (Pugh and Tjian (1990) *Cell* 61:1187–1197; Kelleher et al. (1990) *Cell* 61:1209–1215; Berger et al. (1990) *Cell* 61:1199–1208).

In humans LEF-1 is a general transcription factor that participates in the regulation of the T-cell receptor alpha (TCR alpha) enhancer. The function of LEF 1 is dependent, in part, on a DNA binding domain that helps to induces a sharp bend in the DNA helix, and on an activation domain that stimulates transcription only in a specific context of other enhancer-binding proteins. The ALY transcriptional activator functions in this context-dependent manner and is a novel LEF 1-interacting protein. ALY is a ubiquitously expressed, nuclear protein that specifically associates with the activation domains of LEF-1 and AML-1, which is another protein component of the TCR alpha enhancer complex. In addition, ALY can increase DNA binding by both LEF-1 and AML proteins.

Overexpression of ALY stimulates the activity of the TCR alpha enhancer complex in cells, whereas down-regulation of ALY by anti-sense oligonucleotides virtually eliminates TCR alpha enhancer activity in T cells. Thus, ALY may mediate specific transcriptional activation by facilitating the functional collaboration of multiple proteins in the TCR alpha enhancer complex (Bruhn et al., (1997) *Genes Dev* 11(5):640–653).

Accordingly, the availability of nucleic acid sequences encoding all or a portion of ALY transcription coactivator proteins would facilitate studies to better understand transcription in plants and ultimately provide methods to engineer mechanisms to control transcription.

SUMMARY OF THE INVENTION

The instant invention relates to isolated nucleic acid fragments encoding transcription coactivators. Specifically, this invention concerns an isolated nucleic acid fragment encoding an ALY transcription coactivator and an isolated nucleic acid fragment that is substantially similar to an isolated nucleic acid fragment encoding an ALY transcription coactivator. In addition, this invention relates to a nucleic acid fragment that is complementary to the nucleic acid fragment encoding ALY.

An additional embodiment of the instant invention pertains to a polypeptide encoding all or a substantial portion of an ALY transcription coactivator.

In another embodiment, the instant invention relates to a chimeric gene encoding an ALY transcription coactivator, or to a chimeric gene that comprises a nucleic acid fragment that is complementary to a nucleic acid fragment encoding an ALY transcription coactivator, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an ALY transcription coactivator, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an ALY transcription coactivator in a transformed host cell comprising: a) transforming a host cell with a chimeric gene comprising a nucleic acid fragment encoding an ALY transcription coactivator; and b) growing the transformed host cell under conditions that are suitable for expression of the chimeric gene wherein expression of the chimeric gene results in production of altered levels of ALY in the transformed host cell.

An addition embodiment of the instant invention concerns a method for obtaining a nucleic acid fragment encoding all or a substantial portion of an amino acid sequence encoding an ALY transcription coactivator.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 shows a comparison of the amino acid sequences set forth in SEQ ID NOs:2, 4, 6, 8 and 10 and the *Mus*

*musculus* and *Homo sapiens* sequences (SEQ ID NO:11 and 12 respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Transcription Coactivators

| Protein | Clone Designation | SEQ ID NO: (Nucleotide) | (Amino Acid) |
|---|---|---|---|
| ALY | Contig composed of:<br>cbn10.pk0009.g8<br>p0059.cmsbe14r<br>p0081.chcaa51r | 1 | 2 |
| ALY | rlr24.pk0084.f10 | 3 | 4 |
| ALY | Contig composed of:<br>sdp2c.pk025.m4<br>sls2c.pk011.p22<br>sr1.pk0070.g3 | 5 | 6 |
| ALY | wlk8.pk0016.e6 | 7 | 8 |
| ALY | wlm1.pk0005.c5 | 9 | 10 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several ALY transcription coactivators have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other ALY transcription coactivators, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36: 1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of transcription in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded transcription coactivator. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
| --- | --- | --- |
| cbn10 | Corn (*Zea mays* L.) developing kernel (embryo and endosperm; 10 days after pollination) | cbn10.pk0009.g8 |
| p0059 | Corn (*Zea mays* L.), Germinating maize seeds: two and three days, scutelar node, under normal growth condition | p0059.cmsbe14r |
| p0081 | Corn, (*Zea mays* L.) 10 days after pollination, pedical | p0081.chcaa51r |
| rlr24 | Rice leaf 15 days after germination, 24 hours after infection of strain *Magaporthe grisea* 4360-R-67 (AVR2-YAMO); Susceptible | rlr24.pk0084.f10 |
| sdp2c | Soybean (*Glycine max* L.) developing pods 6–7 mm | sdp2c.pk025.m4 |
| sls2c | Soybean (*Glycine max* L.) infected with *Sclerotinia sclerotiorum* mycelium | sls2c.pk011.p22 |
| sr1 | Soybean (*Glycine max* L.) root library | wr1.pk0070.g3 |
| wlk8 | Wheat (*Triticum aestivum* L.) seedlings 8 hr after treatment with fungicide* | wlk8.pk0016.e6 |
| wlm1 | Wheat (*Triticum aestivum* L.) seedlings 1 hr after inoculation with *Erysiphe graminis* f. sp tritici | wlm1.pk0005.c5 |

*Fungicide: application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding ALY transcription coactivators were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding ALY Homologs

The BLASTX search using the EST sequences from clones listed in Table 3 revealed similarity of the polypeptides encoded by the cDNAs to ALY from *Mus musculus* (NCBI Identifier No. gi 1916290) and *Homo sapiens* (NCBI Identifier No. gi 2896146). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Mus musculus* and *Homo sapiens* ALY Proteins

| Clone | Status | BLAST pLog Score |
| --- | --- | --- |
| Contig composed of: | Contig | 43.00 (gi 1916290) |
| cbn10.pk0009.g8 | | |
| p0059.cmsbe14r | | |
| p0081.chcaa51r | | |
| rlr24.pk0084.f10 | EST | 27.05 (gi 2896146) |
| Contig composed of: | Contig | 34.15 (gi 1916290) |
| sdp2c.pk025.m4 | | |
| sls2c.pk011.p22 | | |
| sr1.pk0070.g3 | | |

TABLE 3-continued

BLAST Results for Sequences Encoding Polypeptides
Homologous to *Mus musculus* and *Homo sapiens* ALY Proteins

| Clone | Status | BLAST pLog Score |
|---|---|---|
| wlk8.pk0016.e6 | EST | 24.00 (gi 1916290) |
| wlm1.pk0005.c5 | FIS | 33.70 (gi 1916290) |

FIG. 1 presents an alignment of the amino acid sequences set forth in SEQ ID NOs:2, 4, 6, 8 and 10 and the Mus musculus and Homo sapiens sequences (SEQ ID NO:11 and 12 respectively). The data in Table 4 represents a calculation of the percent identity of the amino acid sequences set forth in SEQ ID NOs:2, 4, 6, 8 and 10 and the *Mus musculus* and *Homo sapiens* sequences (SEQ ID NO:11 and 12 respectively).

TABLE 4

Percent Identity of Amino Acid Sequences Deduced
From the Nucleotide Sequences of cDNA Clones
Encoding Polypeptides Homologous
to *Mus musculus* and *Homo sapiens* ALY Proteins

| SEQ ID NO. | Percent Identity to |
|---|---|
| 2 | 35% (gi 1916290) |
| 4 | 30% (gi 2896146) |
| 6 | 46% (gi 1916290) |
| 8 | 37% (gi 1916290) |
| 10 | 29% (gi 1916290) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an ALY protein. These sequences represent the first corn, rice, soybean and wheat sequences encoding ALY proteins.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35 S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/

He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 gL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated nucleic acid molecule comprising:
   (a) a nucleotide sequence encoding an ALY transcription coactivator, wherein the amino acid sequence of the coactivator is at least 80% identical to the amino acid sequence of SEQ ID NO:2, SEQ ID NO:4, SEQ ID NO:6, SEQ ID NO:8, or SEQ ID NO:10, or
   (b) the complement of the nucleotide sequence (a).

2. The nucleic acid molecule of claim 1 being RNA.

3. The nucleic acid molecule of claim 1, wherein the amino acid sequence of the coactivator is at least 90% identical to the amino acid sequence of SEQ ID NO:2, SEQ ID NO:4, SEQ ID NO:6, SEQ ID NO:8, or SEQ ID NO:10.

4. The nucleic acid molecule of claim 1, wherein the amino acid sequence of the coactivator is at least 95% identical to the amino acid sequence of SEQ ID NO:2, SEQ ID NO:4, SEQ ID NO:6, SEQ ID NO:8, or SEQ ID NO:10.

5. The nucleic acid molecule of claim 1, wherein the coactivator comprises the amino acid sequence of SEQ ID NO:2, SEQ ID NO:4, SEQ ID NO:6, SEQ ID NO:8, or SEQ ID NO:10.

6. The nucleic acid molecule of claim 1, wherein the nucleotide sequence comprises the nucleotide sequence of SEQ ID NO: 1, SEQ ID NO:3, SEQ ID NO:5, SEQ ID NO:7, or SEQ ID NO:9.

7. An expression vector comprising the nucleic acid molecule of claim 1 operably linked to regulatory sequences suitable for the expression of the nucleotide sequence.

8. An isolated ALY transcription coactivator, wherein the amino acid sequence of the coactivator is at least 80% identical to the amino acid sequence of SEQ ID NO:2, SEQ ID NO:4, SEQ ID NO:6, SEQ ID NO:8, or SEQ ID NO:10.

9. The coactivator of claim 8, wherein the amino acid sequence of the coactivator is at least 90% identical to the amino acid sequence of SEQ ID NO:2, SEQ ID NO:4, SEQ ID NO:6, SEQ ID NO:8, or SEQ ID NO: 10.

10. The coactivator of claim 8, wherein the amino acid sequence of the coactivator is at least 95% identical to the amino acid sequence of SEQ ID NO:2, SEQ ID NO:4, SEQ ID NO:6, SEQ ID NO:8, or SEQ ID NO:10.

11. The coactivator of claim 8 comprising the amino acid sequence of SEQ ID NO:2, SEQ ID NO:4, SEQ ID NO:6, SEQ ID NO;8, or SEQ ID NO:10.

12. A method for transforming a cell comprising transforming a cell with the nucleic acid molecule of claim 1.

13. The cell produced by the method of claim 12.

* * * * *